(12) United States Patent
Ritland

(10) Patent No.: US 6,991,632 B2
(45) Date of Patent: Jan. 31, 2006

(54) ADJUSTABLE ROD AND CONNECTOR DEVICE AND METHOD OF USE

(76) Inventor: Stephen Ritland, 1150 N. San Francisco St., Flagstaff, AZ (US) 86001

( * ) Notice: Subject to any disclaimer, the term of this patent is extended or adjusted under 35 U.S.C. 154(b) by 217 days.

(21) Appl. No.: 10/788,172

(22) Filed: Feb. 25, 2004

(65) Prior Publication Data

US 2004/0181223 A1 Sep. 16, 2004

Related U.S. Application Data

(63) Continuation-in-part of application No. 10/262,574, filed on Sep. 30, 2002.
(60) Provisional application No. 60/325,809, filed on Sep. 28, 2001, provisional application No. 60/450,179, filed on Feb. 25, 2003, and provisional application No. 60/460,195, filed on Apr. 4, 2003.

(51) Int. Cl.
*A61B 17/70* (2006.01)

(52) U.S. Cl. .................................. 606/61; 606/73
(58) Field of Classification Search .............. 606/60, 606/61, 72, 73, 53, 54, 59, 69, 70, 71
See application file for complete search history.

(56) References Cited

U.S. PATENT DOCUMENTS

| | | | |
|---|---|---|---|
| 4,041,939 A | 8/1977 | Hall | 606/61 |
| 4,743,260 A | 5/1988 | Burton | 623/17 |
| 5,002,542 A * | 3/1991 | Frigg | 606/61 |
| 5,002,576 A | 3/1991 | Fuhrmann et al. | 623/17 |
| 5,026,373 A | 6/1991 | Ray et al. | 606/61 |
| 5,030,220 A | 7/1991 | Howland | 606/61 |
| 5,055,104 A | 10/1991 | Ray | 606/61 |
| 5,129,900 A | 7/1992 | Asher et al. | 606/61 |
| 5,275,600 A * | 1/1994 | Allard et al. | 606/61 |
| 5,306,309 A | 4/1994 | Wagner et al. | 623/17 |
| 5,312,405 A | 5/1994 | Korotko et al. | 606/61 |
| 5,415,661 A | 5/1995 | Holmes | 606/69 |
| 5,466,238 A | 11/1995 | Lin | 606/61 |
| 5,474,555 A | 12/1995 | Puno et al. | 606/73 |
| 5,484,440 A | 1/1996 | Allard | 606/73 |
| 5,489,308 A | 2/1996 | Kuslich et al. | 623/17 |
| 5,565,502 A | 10/1996 | Glimcher et al. | 523/115 |

(Continued)

FOREIGN PATENT DOCUMENTS

| | | |
|---|---|---|
| EP | 0 820 731 A1 | 1/1998 |
| WO | WO 03/026523 | 4/1993 |
| WO | WO 02/02022 | 1/2002 |
| WO | WO 03/073908 | 9/2003 |
| WO | WO 03/094699 | 11/2003 |

OTHER PUBLICATIONS

U.S. Appl. No. 10/776,094, filed Feb. 10, 2004, Ritland.

*Primary Examiner*—David O. Reip
(74) *Attorney, Agent, or Firm*—Sheridan Ross P.C.

(57) ABSTRACT

A low-profile surgical rod implant device is provided that allows the length of a rod spanning two bone screws to be adjusted at the time of implantation. In a separate aspect of the invention, the rod implant device can be secured by tightening and securing an end of the rod implant device at one of the bone screws. Embodiments are provided for use with polyaxial pedicle screws and substantially straight shank pedicle screws in spinal applications. In a separate aspect of the invention, a bone screw connector having an interference type fit is also provided. A method for implanting the device is also provided.

23 Claims, 8 Drawing Sheets

U.S. PATENT DOCUMENTS

| | | | |
|---|---|---|---|
| 5,591,166 A | 1/1997 | Bernhardt et al. | 606/61 |
| 5,591,235 A | 1/1997 | Kuslich | 606/61 |
| 5,593,409 A | 1/1997 | Michelson | 606/61 |
| 5,628,740 A | 5/1997 | Mullane | 606/61 |
| 5,643,263 A | 7/1997 | Simonson | 606/61 |
| 5,643,264 A | 7/1997 | Sherman et al. | 606/61 |
| 5,645,599 A | 7/1997 | Samani | 623/17 |
| 5,683,463 A | 11/1997 | Godefroy et al. | 623/17 |
| 5,690,632 A | 11/1997 | Schwartz et al. | 606/73 |
| 5,691,397 A | 11/1997 | Glimcher et al. | 523/115 |
| 5,702,455 A | 12/1997 | Saggar | 623/17 |
| 5,716,415 A | 2/1998 | Steffee | 623/17 |
| 5,725,528 A | 3/1998 | Errico et al. | 606/61 |
| 5,735,899 A | 4/1998 | Schwartz et al. | 623/17 |
| 5,746,741 A | 5/1998 | Kraus et al. | 606/54 |
| 5,752,957 A | 5/1998 | Ralph et al. | 606/61 |
| 5,766,253 A | 6/1998 | Brosnahan, III | 623/17 |
| 5,782,832 A | 7/1998 | Larsen et al. | 606/61 |
| 5,785,710 A | 7/1998 | Michelson | 606/61 |
| 5,800,435 A | 9/1998 | Errico et al. | 606/61 |
| 5,827,328 A | 10/1998 | Buttermann | 623/17 |
| 5,836,948 A | 11/1998 | Zucherman et al. | 606/61 |
| 5,860,977 A | 1/1999 | Zucherman et al. | 606/61 |
| 5,865,847 A | 2/1999 | Kohrs et al. | 623/17 |
| 5,865,848 A | 2/1999 | Baker | 623/17 |
| 5,876,404 A | 3/1999 | Zucherman et al. | 606/61 |
| 5,885,285 A | 3/1999 | Simonson | 606/61 |
| 5,897,593 A | 4/1999 | Kohrs et al. | 623/17 |
| 5,906,616 A | 5/1999 | Pavlov et al. | 606/61 |
| 5,928,233 A | 7/1999 | Apfelbaum et al. | 606/61 |
| 5,968,098 A | 10/1999 | Winslow | 623/17 |
| 5,984,924 A | 11/1999 | Asher et al. | 606/61 |
| 5,997,539 A | 12/1999 | Errico et al. | 606/61 |
| 6,045,579 A | 4/2000 | Hochshuler et al. | 623/17 |
| 6,048,342 A | 4/2000 | Zucherman et al. | 606/61 |
| 6,050,997 A | 4/2000 | Mullane | 606/61 |
| 6,063,088 A | 5/2000 | Winslow | 606/61 |
| 6,068,630 A | 5/2000 | Zucherman et al. | 606/61 |
| 6,074,390 A | 6/2000 | Zucherman et al. | 606/61 |
| 6,074,393 A | 6/2000 | Sitoto | 606/73 |
| 6,080,193 A | 6/2000 | Hochshuler et al. | 623/17 |
| 6,083,225 A | 7/2000 | Winslow et al. | 606/61 |
| 6,090,112 A | 7/2000 | Zucherman et al. | 606/61 |
| 6,102,948 A | 8/2000 | Brosnahan, III | 623/17 |
| 6,113,602 A | 9/2000 | Sand | 606/61 |
| 6,117,137 A | 9/2000 | Halm et al. | 606/72 |
| 6,117,174 A | 9/2000 | Nolan | 623/17.11 |
| 6,120,506 A | 9/2000 | Kohrs et al. | 606/80 |
| 6,123,705 A | 9/2000 | Michelson | 606/61 |
| 6,123,706 A | 9/2000 | Lange | 606/61 |
| 6,132,430 A | 10/2000 | Wagner | 606/61 |
| 6,149,652 A | 11/2000 | Zucherman et al. | 606/61 |
| 6,149,686 A | 11/2000 | Kuslich et al. | 623/17.11 |
| 6,152,926 A | 11/2000 | Zucherman et al. | 606/61 |
| 6,156,038 A | 12/2000 | Zucherman et al. | 606/61 |
| 6,179,838 B1 | 1/2001 | Fiz | 606/61 |
| 6,183,471 B1 | 2/2001 | Zucherman et al. | 606/61 |
| 6,190,387 B1 | 2/2001 | Zucherman et al. | 606/61 |
| 6,190,414 B1 | 2/2001 | Young et al. | 623/17.15 |
| 6,206,922 B1 | 3/2001 | Zdeblick et al. | 623/17.11 |
| 6,206,923 B1 | 3/2001 | Boyd et al. | 623/17.11 |
| 6,224,631 B1 | 5/2001 | Kohrs | 623/17.11 |
| 6,235,030 B1 | 5/2001 | Zucherman et al. | 606/61 |
| 6,238,397 B1 | 5/2001 | Zucherman et al. | 606/61 |
| 6,245,072 B1 | 6/2001 | Zdeblick et al. | 606/61 |
| 6,248,106 B1 | 6/2001 | Ferree | 606/61 |
| 6,261,287 B1 | 7/2001 | Metz-Stavenhagen | 606/61 |
| 6,264,658 B1 | 7/2001 | Lee et al. | 606/61 |
| 6,267,763 B1 | 7/2001 | Castro | 606/61 |
| 6,267,764 B1 | 7/2001 | Elberg | 606/61 |
| 6,267,765 B1 | 7/2001 | Taylor et al. | 606/61 |
| 6,287,343 B1 | 9/2001 | Kuslich et al. | 623/17.11 |
| 6,290,700 B1 | 9/2001 | Schmotzer | 606/61 |
| 6,293,949 B1 | 9/2001 | Justis et al. | 606/61 |
| 6,332,883 B1 | 12/2001 | Zucherman et al. | 606/61 |
| 6,368,350 B1 | 4/2002 | Erickson et al. | 623/17.14 |
| 6,368,351 B1 | 4/2002 | Glenn et al. | 623/17.15 |
| 6,391,058 B1 | 5/2002 | Kuslich et al. | 623/17.11 |
| 6,395,033 B1 | 5/2002 | Pepper | 623/17.13 |
| 6,440,169 B1 | 8/2002 | Elberg et al. | 623/17.16 |
| 6,443,989 B1 | 9/2002 | Jackson | 623/17.15 |
| 6,551,320 B2 | 4/2003 | Lieberman | 606/61 |
| 6,565,569 B1 | 5/2003 | Assaker et al. | 606/61 |
| 6,736,816 B2 | 5/2004 | Ritland | 606/61 |
| 2001/0005796 A1 | 6/2001 | Zdeblick et al. | 623/17.11 |
| 2001/0010021 A1 | 7/2001 | Boyd et al. | 623/17.13 |
| 2001/0047207 A1 | 11/2001 | Michelson | 623/17.11 |
| 2002/0029082 A1 | 3/2002 | Muhanna | 623/17.11 |
| 2002/0068973 A1 | 6/2002 | Jackson | 623/17.11 |
| 2002/0068975 A1 | 6/2002 | Teitelbaum et al. | 623/17.11 |
| 2002/0107571 A1 | 8/2002 | Foley | 623/17.11 |
| 2002/0107572 A1 | 8/2002 | Foley et al. | 623/17.11 |
| 2002/0120270 A1 | 8/2002 | Trieu et al. | 606/61 |
| 2003/0093078 A1 | 5/2003 | Ritland | 606/73 |
| 2003/0144665 A1 | 7/2003 | Munting | 606/61 |
| 2003/0171749 A1 | 9/2003 | Le Couedic et al. | 606/61 |
| 2003/0171751 A1 | 9/2003 | Ritland | 606/61 |
| 2003/0191470 A1 | 10/2003 | Ritland | 606/61 |
| 2004/0002708 A1 | 1/2004 | Ritland | 606/61 |

* cited by examiner

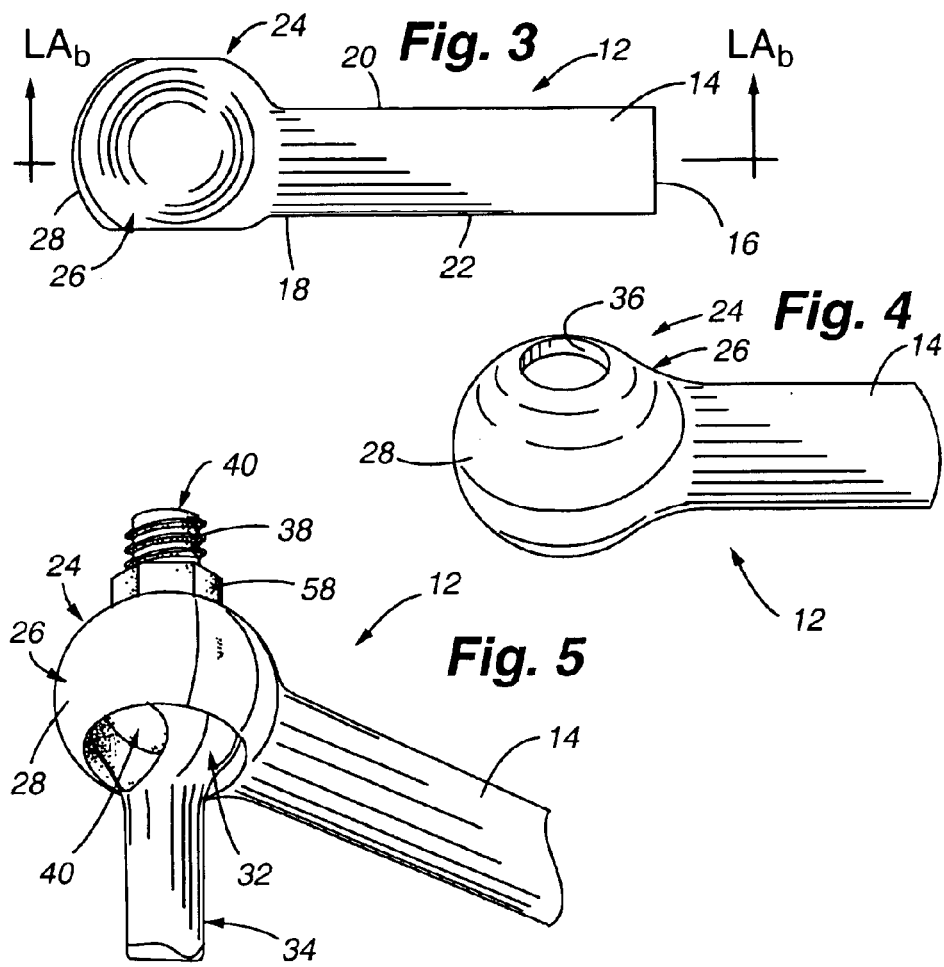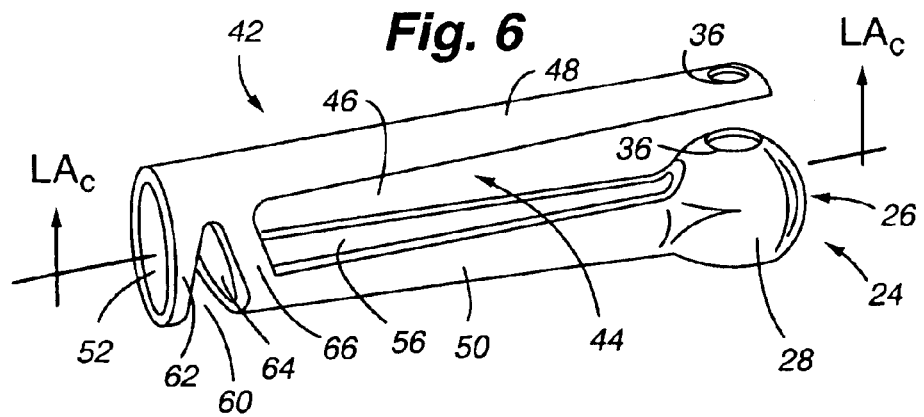

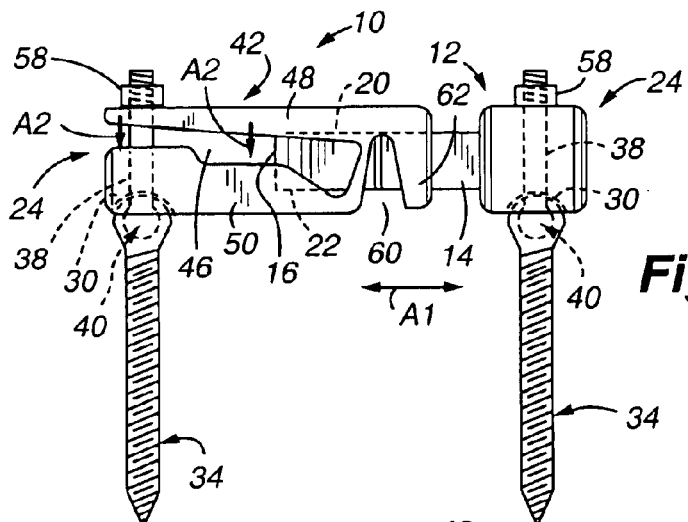
Fig. 7
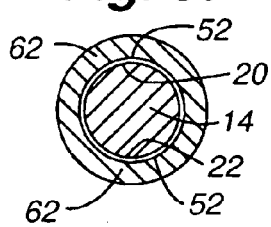
Fig. 8a
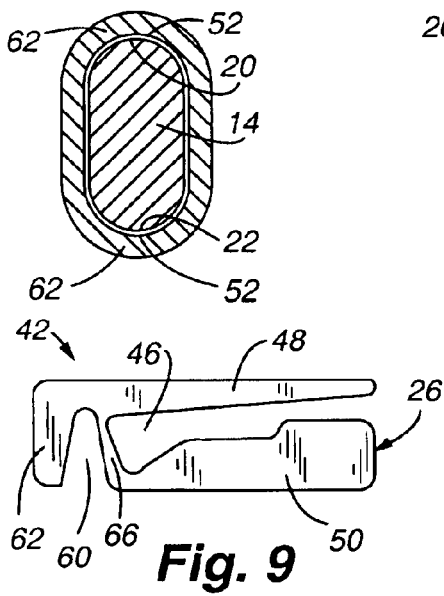
Fig. 8b
Fig. 9
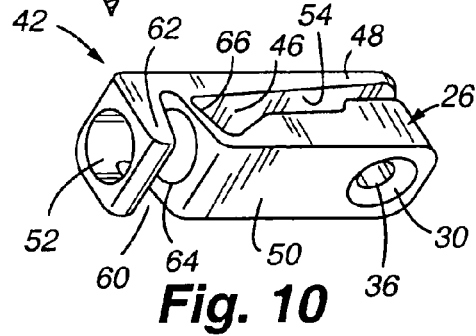
Fig. 10
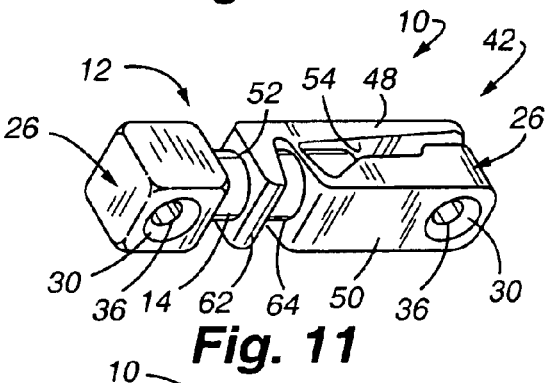
Fig. 11
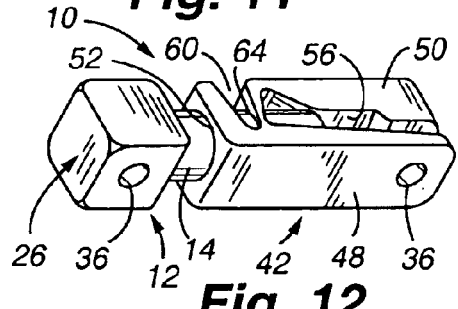
Fig. 12

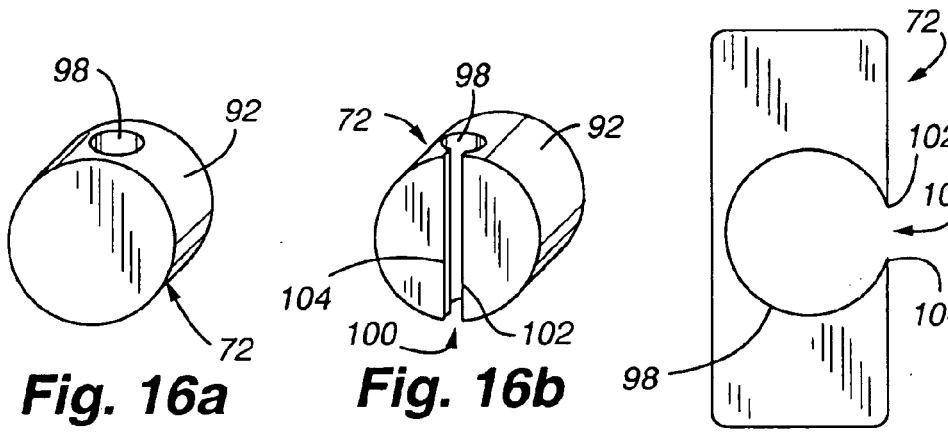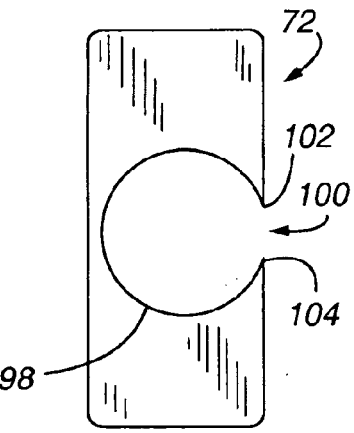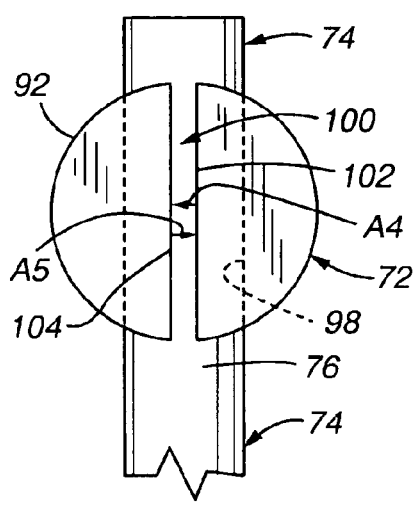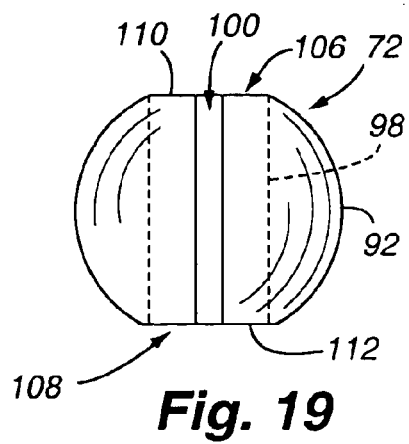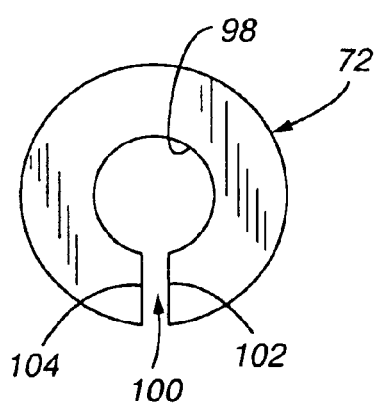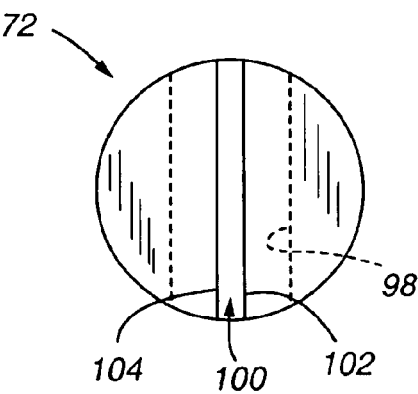

ADJUSTABLE ROD AND CONNECTOR DEVICE AND METHOD OF USE

CROSS REFERENCE AND PRIORITY CLAIMS TO RELATED APPLICATION

This application is a continuation-in-part of, and priority is claimed to, U.S. patent application Ser. No. 10/262,574 filed Sep. 30, 2002, entitled "Connection Rod For Screw or Hook Polyaxial System And Method of Use", which claimed priority to U.S. Provisional Patent Application No. 60/325,809 filed Sep. 28, 2001, entitled "Connection Rod For Screw or Hook Polyaxial System And Method of Use"; priority is also claimed to U.S. Provisional Patent Application No. 60/450,179 filed Feb. 25, 2003 entitled "Connection Rod For Screw or Hook Polyaxial System And Method of Use", and to U.S. Provisional Patent Application No. 60/460,195 filed Apr. 4, 2003 entitled "Sliding Connector". The entire disclosures of these applications are considered to be part of the disclosure of the present application and are hereby incorporated by reference in their entirety. Cross reference is also made to U.S. patent application Ser. No. 09/898,478 filed on Jul. 2, 2001 and entitled "Polyaxial Connection Device and Method," which is also incorporated herein by reference.

FIELD OF THE INVENTION

This invention relates generally to an adjustable rod and connectors for stabilizing a portion of the spine or stabilizing two or more bone segments, and a method of using the same.

BACKGROUND OF THE INVENTION

The use of fixation devices for the treatment of vertebrae deformities and injuries is well known in the art. Various fixation devices are used in medical treatment to correct curvatures and deformities, treat trauma and remedy various abnormal spinal conditions.

The prior art fails to provide a low-profile device that allows the rod length to be easily adjusted during implantation with a minimal amount of effort by the installing surgeon. More particularly, where at least two bones or bone segments are involved, such as a first vertebra and a second vertebra, the rod typically extends beyond the connector, and needs to be specifically chosen or otherwise cut to accommodate the dimensions of the subject patient. Therefore, a need exists to provide an adjustable length rod implantation assembly and component parts that can be installed relatively easily by a surgeon, and that has the ability to be adjusted at the moment of implantation to thereby accommodate the geometry requirements of the patient.

The prior art also fails to provide pedicle screw to rod connectors that can be easily adjusted at the time of implantation. Such devices are needed to further accommodate the individual patient's requirements that exist and that are encountered upon performing and incision and encountering in situ conditions.

In view of the above, there is a long felt but unsolved need for devices and methods that avoid the above-mentioned deficiencies of the prior art and that are relatively simple to employ and require relatively minimal displacement or removal of bodily tissue.

SUMMARY OF THE INVENTION

The present invention addresses the shortcomings of the prior art. More specifically, implant assemblies and/or components of an implant are provided that allow a surgeon to adjust the implant for the patient's requirements as they are encountered during surgery, and/or which allow the surgeon to use low-profile implant components that result in minimal displacement of bodily tissue.

The above and other aspects of the invention are realized in specific illustrated embodiments of the invention, and components thereof. Thus, in one aspect of the present invention, a spinal rod implant for spanning at least one intervertebral disc is provided. The implant is interconnectable to a first vertebra using a first pedicle screw, and to a second vertebra using a second pedicle screw. The first pedicle screw is separated from the second pedicle screw by a bridge distance. The implant comprises a first rod member for interconnecting to the first vertebra, where the first rod member includes a beam having an effective length shorter than the bridge distance. The implant also includes a second rod member for interconnecting to the second vertebra, where the second rod member includes a clamp sized to receive at least a portion of the beam. The clamp also has an effective length shorter than the bridge distance. In addition, the implant includes a means for tightening the clamp to create a force to secure the beam within the clamp.

In a separate aspect of the invention, a surgical implant is provided, where the implant comprises a first rod member including a beam and a second rod member including an opening sized to circumferentially receive the beam. The second rod member also includes an interior hollow chamber for longitudinally receiving at least a portion of the beam. In addition, the second rod member includes an upper arm and an opposing lower arm spaced apart by a slot, wherein the slot is contiguous with the interior hollow chamber. The upper arm is moveable to contact the beam and compress the beam between the upper arm and the lower arm. In addition, the implant includes a means for tightening the second rod member to secure the beam within the second rod member.

A component of the assembly also has application to devices other than a rod implant that is parallel to the spine and that spans an intervertebral disc. For example, the clamp component could be used in bone stabilization unrelated to the spine. Alternatively, it could be used in rod extensions, or it could be adapted for use in cross-link assemblies that are used to structurally interconnect right and left stabilization assemblies that are implanted on either side of a spinous process. Thus, it is one aspect of the present invention to provide a rod member for use with a bone stabilizing rod, the rod member comprising and an upper arm and a lower arm interconnected to the upper arm. At least a portion of the lower arm is separated from the upper arm by a slot and a hollow chamber, where the hollow chamber is sized to receive at least a portion of the bone stabilizing rod. The upper arm is moveable to compress and secure the portion of the bone stabilizing rod between an interior surface of the upper arm and an interior surface of the lower arm.

One embodiment of the present invention features a rod clamping component that can be used in conjunction with a TSRH 3D pedicle screw known to those skilled in the art. The clamping component includes a deformable connector that preferably resides within a cavity in the rod clamping component. The deformable connector has potential application to being used with structures other than pedicle screws. For example, the deformable connector can be used with a properly adapted stabilizing rod that is used for bones other than the spine. Thus, it is one aspect of the present invention to provide a deformable connector for use with a stabilizing rod clamp, the deformable connector capable of securing a portion of a substantially cylindrical member, such as a shank of a TSRH 3D pedicle screw or a stabilizing rod, within a cavity in the stabilizing rod clamp. The deformable connector preferably comprises a disc having a passageway adapted to receive the substantially cylindrical member. In addition, the deformable connector preferably includes a groove along an exterior surface of the disc and extending to the passageway. When compressed within the stabilizing rod clamp, the disc secures the cylindrical member within the passageway.

It is further desirable to provide a low-profile connector that can be easily used in combination with a shank of a bone screw. In a separate embodiment, low profile connector is provided that utilizes an interference-type fit to secure the connector to the shank of the bone screw. Thus, it is one aspect of the present invention to provide a connector device for a bone screw, the connector device comprising a clamp that includes an upper section and a lower section separated by a slot. The upper section includes a first aperture and the lower section includes a second aperture substantially aligned with the first aperture, where the first and second apertures are sized to accommodate a shank of the bone screw. The connector further includes a tightening member operatively connected to the upper section and the lower section. The tightening member tightens the clamp and reduces the size of the slot between the upper section and the lower section. This secures the shank of the bone screw within the device.

It is a further aspect of the present invention to provide a bone stabilization assembly for securing a first bone segment to a second bone segment. This has particular application to being used to bridge an intervertebral disc between two vertebra. The assembly comprises a first bone screw attachable to the first bone segment and a second bone screw attachable to the second bone segment. In addition, the assembly includes a first rod member including a beam and an end connector, where the end connector is attachable to the first bone screw. Also, the assembly includes a second rod member. The second rod member includes an interior hollow chamber for longitudinally receiving at least a portion of the beam of the first rod member. The second rod member includes an upper arm and an opposing lower arm, where the upper arm and the lower arm are spaced apart by a slot, and wherein the slot is contiguous with the interior hollow chamber. The upper arm is moveable and/or deformable to contact the beam and compress the beam between the upper arm and the lower arm. In addition, the second rod member includes a connector attachable to the second bone screw. The assembly also includes a means for tightening the second rod member to secure the beam within the second rod member.

The present invention also includes various methods for using the devices presented herein. One such method concerns stabilizing one or more vertebra using an assembly. Thus, it is one aspect of the present invention to provide a method of stabilizing a first vertebra to a second vertebra. The method comprises the steps of attaching a first pedicle screw to the first vertebra and a second pedicle screw to the second vertebra. In addition, the method includes a step of inserting a beam of a first rod member into a second rod member, where the second rod member includes an interior hollow chamber for longitudinally receiving at least a portion of the beam of the first rod member. The second rod member also includes an upper arm and an opposing lower arm, where the upper arm and the lower arm spaced apart by a slot, and wherein the slot is contiguous with the interior hollow chamber. The upper arm is moveable to contact the beam and compress the beam between the upper arm and the lower arm. In addition, the second rod member includes an integral connector for attaching the second rod member to the second pedicle screw. The method also includes the step of connecting the first rod member to the first pedicle screw using a connector interconnected to the beam. In addition, the method includes the step of advancing a single tightening mechanism to secure (a) the second rod member to the beam of the first rod member, and (b) the second rod member to the second pedicle screw.

Various embodiments of the present invention are set forth in the attached figures and in the detailed description of the invention as provided herein and as embodied by the claims. It should be understood, however, that this Summary of the Invention may not contain all of the aspects and embodiments of the present invention, is not meant to be limiting or restrictive in any manner, and that the invention as disclosed herein is and will be understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

FIG. 3 is a side elevation view of a first embodiment of a first rod member including a beam and an end connector that includes a socket;

FIG. 4 is a perspective view of the device shown in FIG. 3;

FIG. 5 is a perspective view of the device shown in FIG. 3 in combination with a polyaxial pedicle screw and a tension link;

FIG. 6 is a side perspective view of a first embodiment of a second rod member;

FIG. 7 is a reverse side elevation view of a one assembly of the present invention;

FIG. 8a is a cross sectional view along line 8a—8a shown in FIG. 1, wherein the beam has a circular cross section;

FIG. 8b is a cross sectional view along line 8a—8a shown in FIG. 1, wherein the beam has an oblong-shaped cross section;

FIG. 9 is a side elevation view of a second rod member;

FIG. 10 is a bottom perspective view of a second rod member;

FIG. 11 is a bottom perspective view of a first rod member within a second rod member;

FIG. 12 is a top perspective view of a first rod member within a second rod member;

FIG. 16a is a side perspective view of one version of a deformable connector or disc;

FIG. 16b is a side perspective view of a second version of a deformable connector or disc, wherein the disc includes a side grove;

FIG. 17 is a plan view of the device shown in FIG. 16b;

FIG. 18 is a side elevation view of the device shown in FIG. 16b in combination with a pedicle screw having a substantially straight upper shank portion;

FIG. 19 is a side elevation view of a modified version of the device shown in FIG. 16b;

FIG. 20 is a plan view of a yet a different version of the device shown in FIG. 16b, wherein the device of FIG. 20 is spherical in shape rather than disc shaped;

FIG. 21 is a side elevation view of the device shown in FIG. 20;

While the following disclosure describes the invention in connection with those embodiments presented, one should understand that the invention is not strictly limited to these embodiments. Furthermore, one should understand that the drawings are not necessarily to scale, and that in certain instances, the disclosure may not include details which are not necessary for an understanding of the present invention, such as conventional details of fabrication.

DETAILED DESCRIPTION OF THE PREFERRED EMBODIMENT

Figure 1:
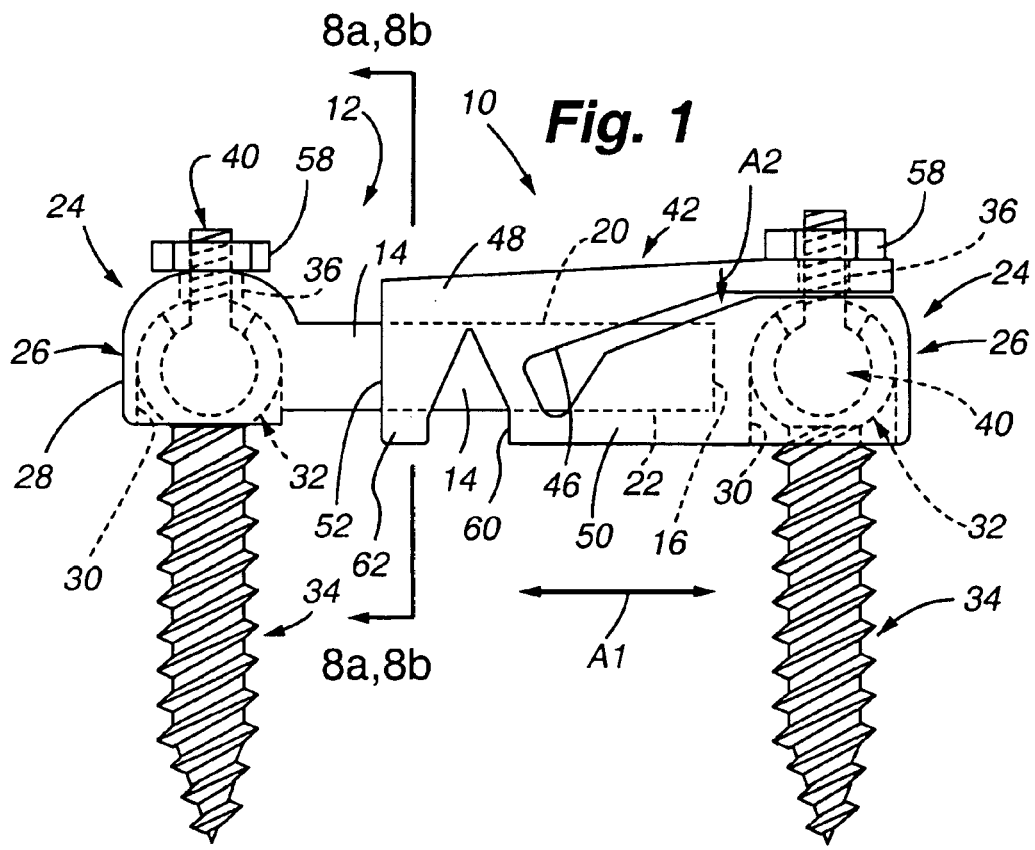
FIG. 1 is a side elevation view of one assembly that incorporates aspects of the present invention, wherein the assembly includes a first embodiment of a first rod member, a first embodiment of a second rod member, polyaxial pedicle screws, tension links, and tension link nuts.
Figure 2:
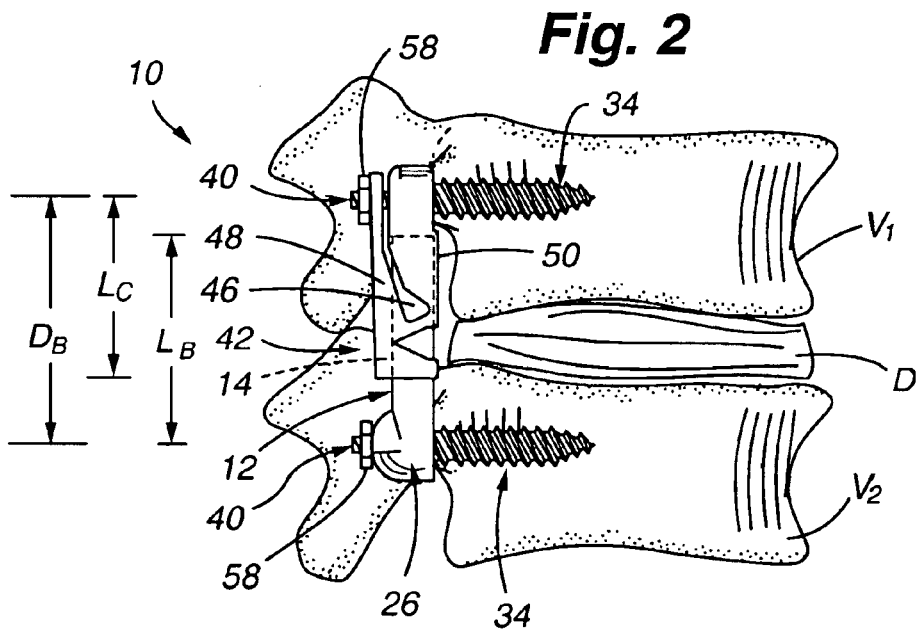
FIG. 2 is a side elevation view of one assembly of the present invention shown after implantation into two vertebra.

Referring to FIG. 1, a first embodiment of an adjustable rod implant 10 is shown. The adjustable rod implant 10 is preferably a multi-piece implant, and more preferably, a two-piece rod implant. By way of example and without limitation, the adjustable rod implant 10 can be used as a structural bridge to span a section of bone, or to span a distance between two portions of bone, or to span a distance between two different bones. As shown in FIG. 2, in one anticipated use, the adjustable rod implant 10 can be used as a vertebral bridge to span at least one intervertebral disc D between two vertebra $V_1$ and $V_2$. Accordingly, by way of illustration and without intending to limit the possible uses of the present invention, the examples of usage presented herein are generally directed toward spanning at least one intervertebral disc.

The adjustable rod implant 10 is preferably attached to the subject vertebrae using pedicle screws, with a connector interconnecting the pedicle screws to the adjustable rod implant 10. The pedicle screws used with the adjustable rod implant 10 may be of a type that allow for some rotational or polyaxial adjustment prior to securing the adjustable rod implant 10, as discussed further below, or the pedicle screws may be of the type that do not allow rotational or polyaxial adjustment. The adjustable rod implant could be used with other types of bone pedicle screws. For example, although not shown, instead of pedicle screws, the rod implant may be used with hook devices that attach to the vertebrae, such hook devices being known to those skilled in the art.

Referring again to FIG. 1, the adjustable rod implant 10 includes a first rod member 12. The first rod member 12 includes a rod or beam 14. As best shown in FIG. 3, the beam 14 has a longitudinal axis $LA_b$—$LA_b$. Beam 14 has a first beam end or distal beam end 16 and a second beam end or proximate beam end 18. The beam 14 also includes a posterior or top side 20 and an anterior or bottom side 22. The beam 14 may have a solid interior or it may have a hollow interior, depending upon the strength requirements of the particular application in which it is being used. For most spinal surgeries, it is anticipated that beam 14 will be solid.

First rod member 12 may be interconnected to a pedicle screw using a separate connector that is not an integral part of first rod member 12. Alternatively, an integral connector may be used. For the embodiment shown in FIG. 1, first rod member 12 includes an end connector 24 attached to the proximate beam end 18 of beam 14. End connector 24 is used to interconnect beam 14 to a pedicle screw. The end connector 24 is preferably incorporated directly into the first rod member 12 in the form of a receptacle 26.

Referring to FIGS. 1 and 3–5, end connector 24 is shown located at the proximate beam end 18 of a beam 14. In a preferred embodiment, the end connector 24 is adjustable and includes a receptacle 26 that is in the form of a socket that preferably includes a socket exterior 28 and a socket interior 30. The socket interior 30 essentially acts as a low-profile connector. The receptacle 26 is sized to fit over and receivingly accept a substantially spherical-headed pedicle screw, such as the enlarged area 32 of a polyaxial pedicle screw 34. Accordingly, socket interior 30 is preferably a recessed area at the proximate beam end 18 of a beam 14 that fits over the enlarged area 32 of the polyaxial pedicle screw 34. As shown in FIGS. 1 and 3–5, the socket interior 30 is preferably nearly spherical, to match a spherical-type shape of enlarged area 32 of the polyaxial pedicle screw 34. However, the socket interior 30 may be a variety of shapes that match the head of the pedicle screw. Within the top center area of the receptacle 26 is a tension link cavity 36 that is sized to accommodate the shaft 38 of a tension link 40. Referring to FIGS. 1 and 4, the tension link cavity 36 can be seen as an opening through the top of receptacle 26.

Referring now to FIG. 3, a side perspective view of the first rod member 12 is shown. The first rod member 12 includes the beam 14 and preferably includes an end connector 24 that is integrally formed with the beam 14, where the end connector 24 is positioned at the second end 18 of the rod member 14. As discussed, the end connector 24 includes structural features the allow the beam 14 to be interconnected to an appropriately configured pedicle screw S.

Referring now to FIG. 4, a top perspective view of the first rod member 12 is shown. For embodiments having an end connector 24, this view illustrates the tension link cavity 36 positioned at substantially the top of the end connector 24 at the proximate beam end 18 of the first rod member 12. The tension link cavity 36 is sized to accommodate the diameter of the shaft 38 of a tension link 40.

Referring now to FIG. 5, a bottom perspective view of the first rod member 12 is shown with an end connector 24, a polyaxial pedicle screw 34, a tension link 40, and a tension link nut 58. The substantially spherical enlarged area 32 of the polyaxial pedicle screw 34 and the substantially spherical socket interior 30 of the end connector 24 allows the end connector 24 to be rotated and adjusted over the enlarged area 32 of a polyaxial pedicle screw 34 before tightening using the tension link nut 58, thus providing adjustability to the rod, connector, and pedicle screw configuration.

When located at the proximate beam end 18 of beam 14, the principal advantage of the integral end connector 24 is to shrink the profile of the configuration as a system, and thereby reduce the length of the rod implant 10 that is longitudinally exposed beyond the pedicle screw location. In so doing, in spinal implant applications, the adjacent vertebra beyond the end of the first rod member 12 is not exposed to potentially impacting a rod section that would have previously extended longitudinally beyond the connector location. This can reduce patient pain and increase patient mobility. A further advantage is that the smaller profile results in less tissue displacement in the vicinity of end connector 24. However, it is again noted that a separate rod to pedicle screw connector known to those skilled in the art may be used to attach a section of rod to a pedicle screw, and therefore, although preferred, and end connector 24 is not required.

Referring again to FIG. 1 and also FIGS. 6 and 9, the second rod member 42 of the adjustable rod implant 10 is shown. The second rod member 42 functions as a clamp, and is preferably a one-piece structure that is deformable to create a compressive force and secure the first rod member 12 within the second rod member 42 when a means for clamping or tightening the second rod member 42 is applied. The second rod member 42 includes an interior hollow chamber 44. The interior hollow chamber 44 is an elongated hollow region having a longitudinal axis $LA_c$—$LA_c$. The interior hollow chamber 44 is sized to accommodate at least a portion of the beam 14 of the first rod member 12.

Referring now to FIG. 10, the second rod member 42 preferably includes a slot 46 that separates an upper arm 48 from a lower arm 50. The lower arm 50 acts as a base for the second rod member 42. The slot 46 forms a gap that can be selectively reduced, whereby the slot 46 allows the upper arm 48 to be selectively deflected toward the lower arm 50.

As best seen in FIG. 10, the second rod member 42 also includes a distal opening 52 that leads to the interior hollow chamber 44. The distal opening 52 is sized to receive the beam 14. More particularly, the distal beam end 16 of beam 14 can be inserted into the distal opening 52, and the beam 14 selectively slid into the interior hollow chamber 44.

Referring to FIGS. 1 and 7, adjustment arrow $A_1$ shows that the beam 14 may be moved from right to left and from left to right within the interior hollow chamber 44 of the second rod member 42 prior to applying a clamping or tightening force to the second rod member 42. The length of the beam 14 that is slid into the interior hollow chamber 44 can be adjusted by the surgeon. FIGS. 11 and 12 show two different perspective views of the beam 14 of the first rod member 12 positioned within the hollow chamber 44 of the second rod member 42. Since the overall length of the implant 10 can be adjusted at the time of the implantation by the surgeon, this allows the surgeon to readily accommodate a patient's particular needs.

By application of a clamping or tightening force to the second rod member 42, the upper arm 48 and lower arm 50 are compressed toward each other, thereby securing the beam 14 within the second rod member 42. In the preferred embodiment shown in FIG. 1, the base or lower arm 50 remains substantially immobile, and the upper arm 48 is deflected toward the lower arm 50. Arrows $A_2$ of FIGS. 1 and 7 show that the upper arm 48 is forced toward the lower arm 50. That is, the upper arm 48 acts as a moveable and/or deformable structure that is suspended over the interior hollow chamber 44, and which can be forced toward the lower arm 50. In so doing, at least a portion of the interior surface 54 of the upper arm 48 applies a compressive force to the top side 20 of the beam 14. The beam 14 then presses downward such that the bottom side 22 of the beam 14 presses against the interior surface 56 of the base or lower arm 50 of the second rod member 42. This interaction of forces causes the beam 14 to be compressively secured within the second rod member 42.

Referring again to FIG. 1, similar to first rod member 12, the second rod member 42 preferably includes an end connector 24 attached to lower arm 50 of the second rod member 42. The end connector 24 is used to interconnect the second rod member 42 to a polyaxial pedicle screw 34. The end connector 24 is preferably incorporated directly into the second rod member 42 in the form of a receptacle 26. When located at the end of the second rod member 42, the principal advantage of the integral end connector 24 is to shrink the profile of the configuration as a system, and thereby reduce the length of the rod implant 10 that is longitudinally exposed beyond the pedicle screw location. In so doing, in spinal implant applications, the adjacent vertebra beyond the end of the second rod member 42 is not exposed to potentially impacting a rod section that would have previously extended longitudinally beyond the connector location. This can reduce patient pain and increase patient mobility. A further advantage is that the smaller profile results in less tissue displacement in the vicinity of the end connector 24.

The structure of the end connector 24 for the second rod member 42 is similar to that for the first rod member 12. However, both the upper arm 48 and lower arm 50 of the second rod member 42 include a tension link cavity 36 that is sized to accommodate the shaft 38 of the tension link 40. Referring to FIG. 1, the tension link cavity 36 can be seen as an opening through the top of the end of the upper arm 48, where the tension link cavity 36 in the upper arm 48 is aligned with the tension link cavity 36 in the lower arm 50. The pedicle screw to be connected to the second rod member 42 is preferably fitted with a tension link 40, and the tension link shaft 38 is extended through the tension link cavity 36 in the receptacle 26 and through the tension link cavity 36 in the upper arm 48. A tension link nut 58 is then threaded onto the end of the tension link shaft 38 and is tightened. The tension link nut 58 provides the tightening or clamping force for the second rod member 42, thereby deflecting the upper arm 48 toward the lower arm 50 and securing the beam 14 within the second rod member 42.

Referring again to FIG. 1, preferably, a notch 60 is positioned in the second rod member 42 near the distal opening 52. For those embodiments incorporating a notch 60, the distal opening 52 next to the notch 60 is essentially a hoop structure 62 through which the beam 14 passes to enter the interior hollow chamber 44. The notch 60 longitudinally separates the distal opening 52 from a second opening or interior opening 64. The interior opening 64 is formed by an arch 66 extending from and interconnecting the upper arm 48 to the lower arm 50.

As shown in FIGS. 1, 2 and 7, in a side elevation view, the notch 60 may be a variety of shapes, such as an inverted U-shape, or an inverted V-shape. Although not required, the hoop structure 62 of the distal opening 52 aligns and supports the beam 14 when it is positioned within the interior hollow chamber 44 prior to tightening of the second beam member 42. The hoop structure 62 of the distal opening 52 also functions to prevent the beam 14 from rocking up and down prior to applying a clamping or tightening force to the second rod member 42. More particularly, the hoop structure 62 substantially maintains the alignment of the longitudinal axis $LA_b$—$LA_b$ of the beam 14 with the longitudinal axis $LA_c$—$LA_c$ of the hollow chamber 44 of the second rod member 42 while sliding the beam 14 into the second rod member 42 and implanting the rod implant 10, and through such time as a clamping or tightening force is applied to the second rod member 42. The notch 60 also serves to lighten the second rod member 42 by reducing its mass.

The beam 14 and the second rod member 42 work in combination to provide an adjustable rod segment that can be shortened or lengthened during the implant procedure by the surgeon to accommodate the specific spacial requirements of the patient. One particular use of the implant is to span one level (one intervertebral disc). Referring to FIG. 2, in use, the surgeon first inserts a first pedicle screw 34 into a first vertebra $V_1$ of the patient, and then inserts a second pedicle screw 34 into a second vertebra $V_2$ of the patient. Tension links 40 are then inserted into the enlarged areas 32 of the pedicle screws 34. Alternately, the tension links are preloaded into the pedicle screws before they are implanted into the vertebrae. The beam 14 is then interconnected to the first pedicle screw 34 using a first connector, and the second rod member 42 is interconnected to the second pedicle screw 34 using a second connector. To perform this step, the beam 14 is preferably loosely inserted into the second rod member 42 in advance of interconnecting the second rod member 42 to the second pedicle screw. That is, the surgeon preassembles the beam 14 of the first rod member 12 inside the second rod member 42, but does not tighten the two members together. The surgeon then lowers both the first rod member 12 and the second rod member 42 as a unit over the pedicle screws. Referring again to FIGS. 1 and 2, the surgeon then preferably tightens a link nut 58 over the tension link shaft 38 that is associated with the first rod member 12. Again, the surgeon may then adjust the length of the beam 14 inside the second rod member 42 by sliding the beam 14 into or out of the clamp to obtain the proper bridge distance needed between the first pedicle screw and the second pedicle screw. Subsequently, the surgeon can apply a tightening force to the second rod member 42 to secure the beam 14 within the second rod member 42. The implant 10 provides the surgeon the ability to tighten the second rod member 42 to its associated pedicle screw and also clamp the second rod member 42 to the first rod member 12 using one effort and one structure. This is accomplished in the preferred assembly shown in FIGS. 1 and 2 by applying and tightening a link nut 58 to the tension link shaft 38 of the tension link 40, which is operatively connected to the enlarged area 32 of the pedicle screw 34 associated with the second rod member 42. This action progressively and selectively deflects the upper arm 48 toward the lower arm 50, thereby compressively securing the beam 14 of the first rod member 12 within the second rod member 42.

Referring now to the preferred embodiment shown in FIG. 2, and for purposes of this description, an effective beam length $L_b$ of beam 14 is defined as the distance from the pedicle screw to which it is attached to the distal beam end 16. The effective clamp length $L_c$ of second rod member 42 is defined as the distance from the pedicle screw to which it is attached to the distal opening 52. For the assembly shown in FIG. 2, both the effective beam length $L_b$ and the effective clamp length $L_c$ are shorter than the bridge distance $D_B$, which is the distance between the first pedicle screw and the second pedicle screw.

Referring now to FIG. 3, rotational adjustability of the implant 10 can be provided by using a beam 14 that is rotatable within the interior hollow chamber 44. For example, a beam 14 having a circular cross section like that shown in FIG. 8a can be coupled with a second rod member 42 preferably having a circular distal opening 52 and interior hollow chamber 44. In this example, the circular cross section of beam 14 maybe rotated within the second rod member 42, thereby allowing the surgeon the ability to rotate and angularly adjust the position of the first rod member 12 relative to the second rod member 42. Rotational adjustability is permitted before applying a tightening force to the second rod member 42 and securing the beam 14 within the interior hollow chamber 44 of the second rod member 42. FIG. 8b illustrates that beam 14 may have a cross section resembling an oblong shape. For this variation, the distal opening 52 and interior hollow chamber 44 are also preferably substantially oblong in shape. This modification provides an assembly that does not allow rotation of the first rod member 12 relative to the second rod member 42, which may be desirable in certain situations. Of course, other configurations are possible, such as corresponding triangular, rectangular, and polygonal shapes (not shown). In addition, the beam cross-section may differ from the shape of the cross-section of the interior hollow chamber. Thus, a variety of shapes and combination of shapes are possible for the cross section of the beam 14 and the interior hollow chamber 44, and such possible different shapes for the structures are within the scope of the present invention.

Figure 13:
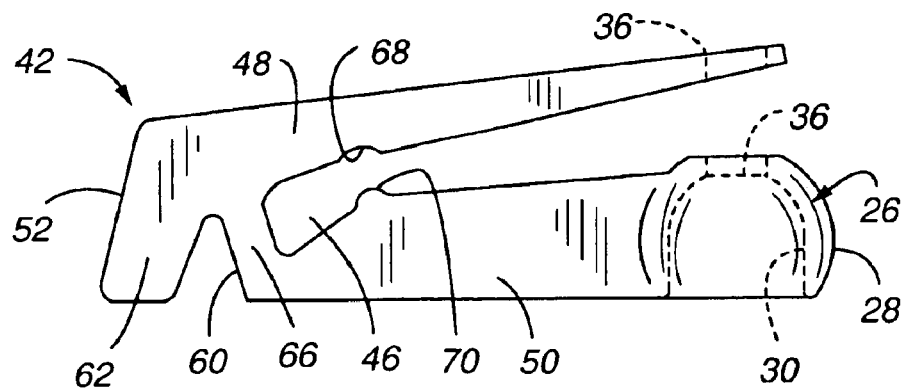
FIG. 13 is a side elevation view of a second rod member having a recess on its upper arm and projection on its lower arm.

Referring now to FIG. 13, the upper arm 48 of the second rod member 42 may optionally include a recess 68 for receiving a cooperating projection 70 positioned on the edge of the slot of the lower arm 50. The recess 68 and projection 70 may be a variety of shapes, and may include means for interlocking. For example, the projection 70 may include a barb (not shown) that interlocks with one or more ridges (not shown) within the recess 68. The position of the recess 68 and projection 70 may be reversed such that the recess is located on the lower arm 50 and the projection is located on the upper arm 48.

Referring to FIGS. 1–13, the socket exterior 28 of the end connector 24 at one or both of the first rod member 12 and second rod member 42 maybe rounded to substantially mirror the socket interior 30 as shown in FIG. 1. Alternatively, it may be have a different shape, such as the block shape shown in FIG. 7. Additionally, as shown in FIG. 1, the center of the enlarged areas 32 of the polyaxial pedicle screws 34 may be substantially aligned with the longitudinal axis of the beam 14 of the first rod member 12, and aligned with the longitudinal axis of the hollow chamber 44 of the second rod member 42, or the centers may be offset, as shown in FIG. 7.

In general, amongst its possible uses, the rod implant 10 permits a length of rod to be adjusted at the surgical site without having to cut the rod, or use a standardized rod length that may not fit the patient. Furthermore, utilizing the components of the present invention, the entire assembly can be tightened by securing a link nut 58 at the second rod member 42. This greatly simplifies the surgeon's efforts and serves to reduce operation time and associated patient risk. In addition, as will be appreciated by those skilled in the art, among its many potential uses the second rod member 42 can be used to attach a new section of rod to an existing section of rod, to extend a section of rod, to provide length adjustability to a rod, to provide a means of attaching a separate structure to the end of a new or existing rod, to provide a means of attaching a separate structure to the end of a new or existing rod while adjusting the length of the rod, or to reinforce an existing section of rod.

Figure 14:
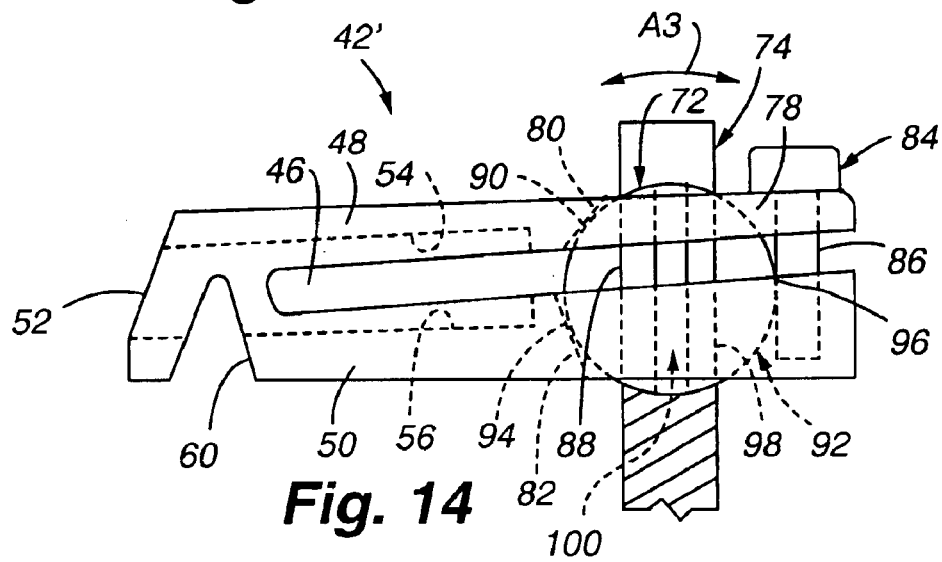
FIG. 14 is a side elevation view of a second embodiment of a second rod member that includes a deformable connector.

Referring now to FIG. 14, a further embodiment of the second rod member 42' is shown. Second rod member 42' includes a number of structural features that are similar to the previously described second rod member 42. That is, an interior hollow chamber 44 is sized to receive a beam 14 of a first rod member 12, and the second rod member 42' functions as a clamp to provide a compressive force to secure the beam 14 of the first rod member 12 within the interior hollow chamber 44. Second rod member 42' differs from second rod member 42 in that it includes a deformable connector 72 that can be used to secure the second rod member 42' to a pedicle screw, wherein the pedicle screw has a substantially straight upper shank portion, such as a TSRH 3D pedicle screw 74 known to those skilled in the art. More particularly, the deformable connector 72 acts as a clamp within a clamp, by providing a compressive force around a portion of the shank 76 of a pedicle screw 74.

Referring still to FIG. 14, the deformable connector 72 is situated within an open portion or cavity 78 of the second rod member 42'. The upper arm 48 of the second rod member 42' preferably includes a upper arm shoulder 80 against which a portion of the deformable connector 72 is positioned. Similarly, the lower arm 50 of the second rod member 42' preferably includes a lower arm shoulder 82, also against which a portion of the deformable connector 72 is positioned. In addition, the second rod member 42' includes a tightening member 84 that serves as a means for tightening the second rod member 42' such that the second rod member 42' compresses and acts as a clamp to hold the beam 14 of the first rod member 12 secure.

In one preferred embodiment, tightening member 84 is a screw or bolt positioned on a substantially opposing side of the deformable connector 72 relative to the positions of the upper arm shoulder 80 and the lower arm shoulder 82. That is, the tightening member 84 is preferably on one side of the shank 76 of the pedicle screw 74, and the upper arm shoulder 80 and the lower arm shoulder 82 are on situated on an opposing side of the shank 76 of the pedicle screw 74. When tightened, the tightening member 84 not only draws the upper arm 48 and the lower arm 50 together, thereby compressing the second rod member 42', but also necessarily shrinks the size of the cavity 78 and consequently confines the deformable connector 72 between the upper arm shoulder 80, the lower arm shoulder 82 and a shank 86 of the tightening member 84. When fully tightened, the tightening member 84 puts at least a first point 90 of the perimeter 92 of the deformable connector 72 in contact with the upper arm shoulder 80. In addition, when fully tightened, the tightening member 84 puts at least a second point 94 of the perimeter 92 of the deformable connector 72 in contact with the lower arm shoulder 82. In addition, the shank 86 of the tightening member 84 contacts at least a third point 96 on the perimeter 92 of the deformable connector 72. These at least three points 90, 94, and 96 compress the deformable connector 72 such that it securely holds the shank 76 of the pedicle screw 74. Preferably, at least one of the upper arm shoulder 80 and the lower arm shoulder 82 are not parallel to a side surface 88 of the shank 76 of the pedicle screw 74.

Figure 15:
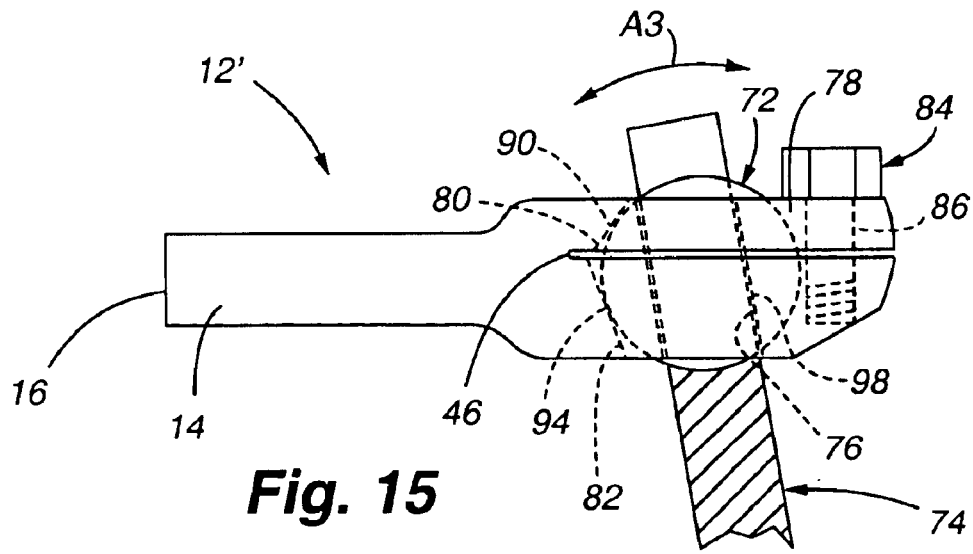
FIG. 15 is a side elevation view of a second embodiment of a first rod member that includes a deformable connector.

Referring now to FIG. 15, the deformable connector 72 may also be adapted for use in a first rod member 12', wherein the first rod member 12' includes a beam 14 that is connected to a pedicle screw 74 by way of the deformable connector 72 that is situated within a cavity 78 of the first rod member 12'. Here, the deformable connector 72 is again confined within the first rod member 12' by a upper arm shoulder 80 and lower arm shoulder 82, and further by the shank 86 of the tightening member 84.

Referring to FIGS. 14 and 15, one advantage to a substantially cylindrical-shaped deformable connector 72 is that it can be rotated within the cavity 78 prior to tightening to accommodate the position of the pedicle screw 74. Therefore, second rod member 42' with deformable connector 72 overcomes the problem of where the pedicle screw 74 is not aligned sufficiently perpendicular to the intend rod axis. A substantially cylindrical-shaped deformable connector 72 can be rotated within the cavity 78 and then slipped over the shank 76 of the pedicle screw 74, and subsequently secured within the second rod member 42' by tightening the tightening member 84. Thus, deformable connector 72 in combination with a clamping style first rod member 12' or second rod member 42' is rotatably adjustable prior to tightening. Rotation arrows $A_3$ illustrate that the deformable connector 72 is rotatable within the cavity 78. This allows a surgeon to accommodate a patient's particular needs during the surgical procedure.

For the devices shown in FIGS. 14 and 15, and assuming that at least one of either first rod member 12' or second rod member 42' is being used, in use, a surgeon first installs a bone screw for general applications, or a pedicle screw if the device is to be interconnected to the pedicle of a vertebra. Assuming the device is used in an assembly for bridging an intervertebral disc, a second pedicle screw is attached to the other vertebra, or an existing second pedicle screw is used. Alternatively, the device could be used where two existing pedicle screws were already in place. The surgeon then preferably inserts the beam of the first rod member into the second rod member. Subsequently, the surgeon preferably lowers the first rod member and second rod member as a unit over the pedicle screws. The shank 76 of the pedicle screw 74 associated with first rod member 12' or second rod member 42' is slipped into the passageway 98 of the deformable connector 72 that is positioned in the cavity 78 of the respective first rod member 12' or second rod member 42'. The deformable connector 72 is rotated as desired by the surgeon to obtain the proper alignment in order to slip the first rod member 12' or second rod member 42' over the pedicle screw 74. If first rod member 12' is being used, then the surgeon tightens first rod member 12' to its pedicle screw by advancing the tightening member 84 associated with the first rod member 12'. If first rod member 12' is not being used, then the rod member opposite the second rod member 42' is preferably otherwise secured to its pedicle screw. Subsequently, after adjusting the length of the beam 14 within the second rod member, the second rod member is then secured to the first rod member. If second rod member 42' is being used, then the securing step is accomplished by advancing the tightening member 84 associated with the second rod member 42'.

Referring now to FIGS. 16–19, in one preferred embodiment, the deformable connector 72 is substantially cylindrical in shape, and this shape allows the cylindrical deformable connector 72 to rotate within the cavity 78 of the second rod member 42'. The deformable connector 72 includes a passageway 98 for receiving the shank 76 of the pedicle screw 74. More particularly, the passageway 98 is an opening through the deformable connector 72 that is sized to accommodate the shank 76 of a pedicle screw 74. In addition, the deformable connector 72 has a composition or structure allowing the deformable connector 72 to compress around the shank 76 of the pedicle screw 74 upon tightening of the second rod member 42'. More particularly, as shown in FIG. 16a, the deformable connector 72 may be made of a type of material that can be compressed, such as a suitable resilient material. In use, upon tightening the tightening member 84, the deformable connector 72 is squeezed and compressed between the upper arm shoulder 80, lower arm shoulder 82 and the shank 86 of the tightening member 84 such that the shank 76 of the pedicle screw 74 is secured within the deformable connector 72, which in turn, is secured within the second rod member 42'.

Alternatively, as shown in FIGS. 16b, 17, and 18, in a preferred embodiment, the deformable connector 72 may include a slit or groove 100 along a side that preferably intercepts the passageway 98. The groove includes a first edge 102 and an opposing and separated second edge 104. In use, upon tightening the tightening member 84, the deformable connector 72 is squeezed and compressed between the upper arm shoulder 80, lower arm shoulder 82 and the shank 86 of the tightening member 84. The first edge 102 of the groove 100 is moved in a direction of arrow $A_4$ toward the second edge 104, which is being moved in a direction of arrow $A_5$ toward first edge 102. As a result of the tightening force, the groove 100 allows the passageway 98 of deformable connector 72 to collapse around the shank 76 of the pedicle screw 74, such that the pedicle screw 74 is secured within the deformable connector 72, which in turn, is secured within the second rod member 42'.

The deformable connector 72 is anticipated to have a diameter of approximately 10 to 13 mm, and the passageway 98 within the deformable connector 72 is anticipated to have a diameter just slightly larger than the diameter of the shank 76 of a pedicle screw 74, which is typically on the order of about 5.2 mm in size.

Referring now to FIG. 19, for the case of a substantially cylindrical-shaped deformable connector 72, portions of the deformable connector 72 maybe truncated to reduce the weight and displacement volume of the deformable connector 72. For example, a truncated first end 106 and/or a truncated second end 108 of the deformable connector 72 can be flattened or otherwise modified in shape. Preferably, the truncated first end 106 and truncated second end 108 are located at the passageway openings 110 and 112, respectively.

Referring now to FIGS. 20 and 21, the deformable connector 72 may also take the form of a bead or sphere. A sphere-shaped deformable connector 72 allows the deformable connector 72 to be rotated in a multitude of directions to accommodate alignment with the shank 76 of a pedicle screw 74.

Figure 22:
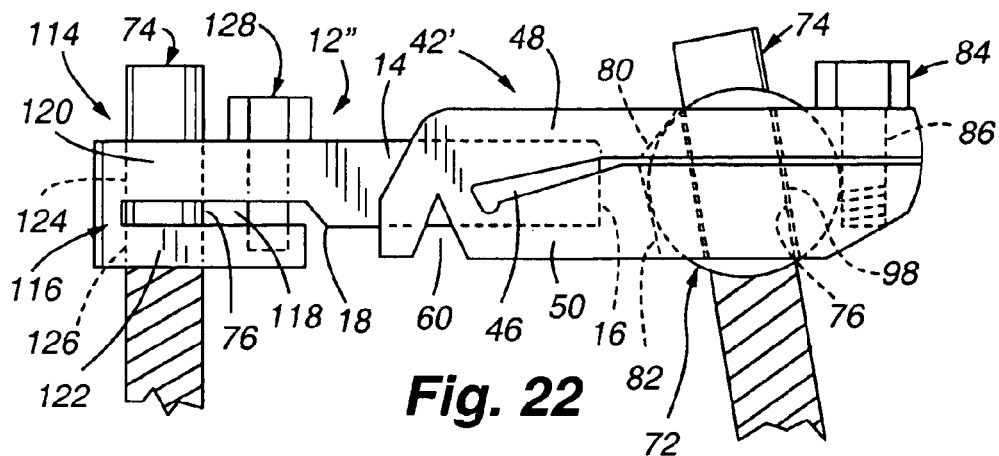
FIG. 22 is a side elevation view of one assembly that incorporates aspects of the present invention, wherein the assembly includes a third embodiment of a first rod member, a second embodiment of a second rod member.

Referring now to FIG. 22, in a separate aspect of the invention, an interference fit connector 114 is presented. For purposes of illustration, a second rod member 42' is shown in combination with a first rod member 12", wherein first rod member 12" incorporates an interference fit connector 114. For the embodiment shown in FIG. 22, the interference fit connector 114 is integrally attached to the beam 14. More particularly, the proximate beam end 18 of first rod member 12" is attached to an interference fit connector 114.

Figure 23:
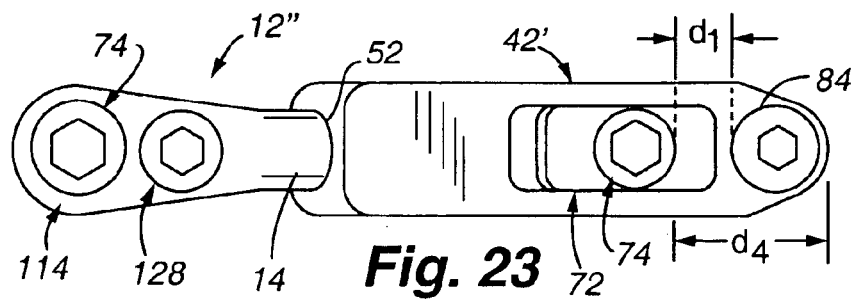
FIG. 23 is a plan view of the assembly shown in FIG. 22.
Figure 24:
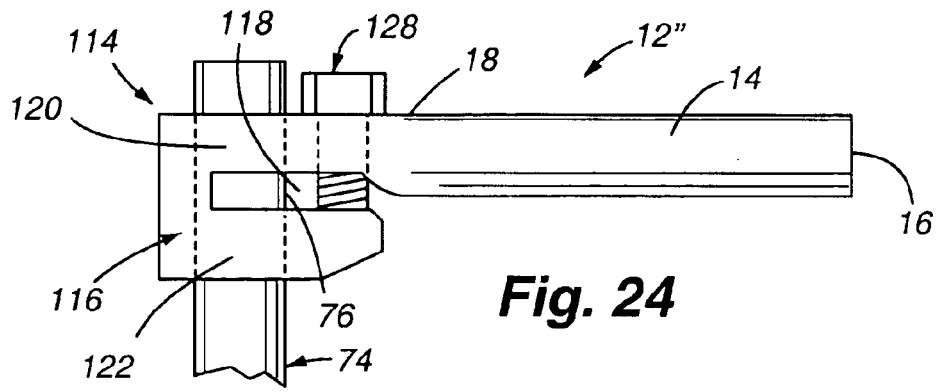
FIG. 24 is a side elevation view of the third embodiment of a first rod member shown in FIG. 22.
Figure 25:
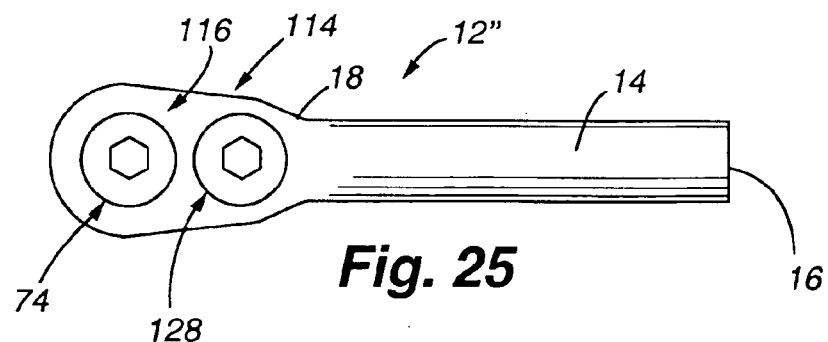
FIG. 25 is a plan view of the device shown in FIG. 24.

Referring now to FIGS. 22–25, interference fit connector 114 has a C-shaped section 116 having a slot 118 separating an upper section 120 from a lower section 122. The first rod member 12" includes a first aperture 124 through the upper section 120, and a second aperture 126 through the lower section 122. In addition, the C-shaped section 116 includes an interference tightening member 128, which serves as a means for tightening the C-shaped section 116 and drawing the upper section 120 and the lower section 122 in closer proximity relative to each other, such that the shank 76 of pedicle screw 74 is pinched or clamped within the C-shaped section 116 and secured to the first rod member 12". As shown in FIGS. 22 and 24, the interference tightening member 128, or means for tightening the C-shaped section 116, can preferably take the form of a screw or a bolt. However, a band clamp, such as a worm-gear band could also be used to compress the upper section 120 and lower section 122 toward each other. Accordingly, a number of means for tightening the C-shaped section 116 are possible and are within the scope of the present invention.

One advantage of the C-shaped section 116 is that, when used in a first rod member 12", it provides a rod and connector combination that is relatively easy for the surgeon to use. A second advantage is that it limits the length of the connector and implant structure that is longitudinally exposed beyond the pedicle screw 74 location. In so doing, in spinal implant applications, the adjacent vertebra beyond the end of the first rod member 12" is not exposed to potentially impacting a rod section that would have previously extended longitudinally beyond the connector location. This can reduce patient pain and increase patient mobility. A further advantage is that the smaller profile results in less tissue displacement in the vicinity of C-shaped section 116.

Figure 26:
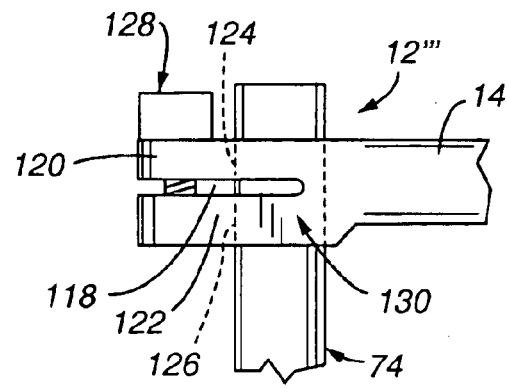
FIG. 26 is a side elevation view of separate embodiment of the device shown in FIG. 24.

Referring now to FIG. 26, a modified version of the device shown in FIG. 24 is presented. The first rod member 12''' shown in FIG. 26 incorporates an integral connector that uses an interference fit, but has a reverse orientation as compared to the device shown in FIG. 24. More specifically, the proximate end 18 of first rod member 12''' includes a reverse C-shaped section 130 having a slot 118 separating an upper section 120 from a lower section 122. The first rod member 12''' includes a first aperture 124 through the upper section 120 and a second aperture 126 through the lower section 122. In addition, the reverse C-shaped section 130 includes an interference tightening member 128, which serves as a means for tightening the reverse C-shaped section 130 and drawing the upper section 120 and the lower section 122 in closer position relative to each other, such that the shank 76 of pedicle screw 74 is clamped or pinched within the reverse C-shaped section 130 and secured to the first rod member 12'''. As shown in FIG. 26, the interference tightening member 128, or means for tightening the reverse C-shaped section 130, can preferably take the form of a screw or a bolt. However, a band clamp, such as a worm-gear band could also be used to compress the upper section 120 and lower section 122 toward each other. Accordingly, a number of means for tightening the C-shaped section 130 are possible and are within the scope of the present invention.

One advantage of the reverse C-shaped section 130 is that, when used in a first rod member 12''', it provides a rod and connector combination that is relatively easy for the surgeon to use. A second advantage is that it provides an interference type of connector fitting where the tightening member 128 is positioned on the opposite side of the pedicle screw 74 as that of the rod portion. Therefore, one potential use is for short bridge distances; that is, where the distance between pedicle screws is relatively small, and does not lend itself to placing the tightening member 128 in a position between the pedicle screws being spanned.

In use, a surgeon first installs a pedicle screw, or otherwise identifies an existing bone screw that the interference fit connector is to be attached to. Depending upon the choice of the device by the surgeon, the surgeon then slips the C-shaped section 116 or the reverse C-shaped section 130 over the shank 76 of the pedicle screw 74. To tighten the type C-shaped section 116 or the reverse C-shaped section 130 to the pedicle screw 74, the surgeon advances the tightening member 128. If a screw or bolt is used as a tightening member 128, this last step comprises advancing the screw or bolt until the C-shaped section 116 or the reverse C-shaped section 130 is secured to the shank 76 of the pedicle screw 74.

An interference fit connector can also be oriented at any angle relative to the beam that is between the pedicle screws. More particularly, FIG. 26 illustrates a reverse C-shaped section 130 that is situated at an angle of about 180 degrees relative to the C-shaped section 116 shown in FIG. 24. That is, it is not on the same side as the beam 14, but instead, it is on the opposite side of the pedicle screw relative to the beam 14. However, the C-shaped connector could be oriented at any angle, such as 30, 45, 60, 90, 135, etc. degrees (not shown) relative to the beam 14 to which it is attached. These different orientations for the C-shaped connector may be preferred depending upon a patient's needs, for example, because of an injury that makes such an orientation preferable.

Figure 27:
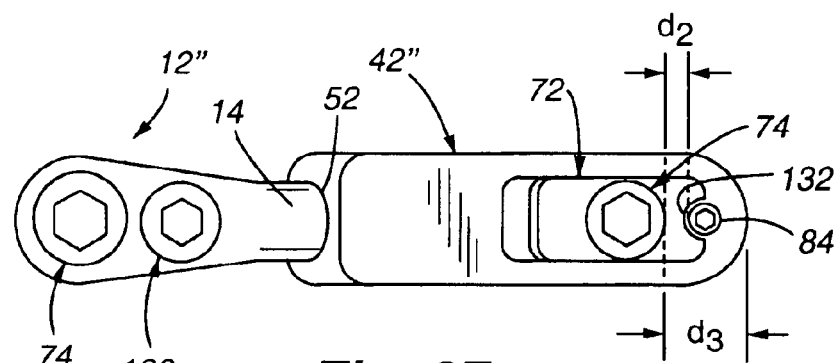
FIG. 27 is a plan view of an assembly having a second embodiment of the second rod member, wherein the deformable connector of the second rod member has an indentation that cooperates with the tightening member.

Referring now to FIG. 27, an implant assembly is shown in plan view that includes two pedicle screws with an interference fit type of integral connector such as first rod member 12" shown on the left side, and a second rod member 42" with a deformable connector 72 shown on the right side. However, the deformable connector 72 of FIG. 27 includes a modified shape in the form of an indentation 132 that cooperates with the tightening member 84. The indentation 132 in the deformable connector 72 extends down the side of the deformable connector 72. The indentation 132 allows the distance $d_2$ between the right-most pedicle screw 74 and the right-most tightening member 84 to be reduced relative to the distance $d_1$ between the right-most pedicle screw 74 and the right-most tightening member 84 as shown in FIG. 23. Said differently, distance $d_1$ of FIG. 23 is less than distance $d_2$ of FIG. 27. This can be further reduced by using a screw as a tightening member 84 that has no upper flange. As a result of the indentation 132 feature, the distance $d_3$ of the length of the second rod member 42" between the right-most pedicle screw 74 and the right-most end of the second rod member 42" is also reduced relative to the distance $d_4$ of the length of the second rod member 42' between the right-most pedicle screw 74 and the right-most end of the second rod member 42', as shown in FIG. 23. For spinal implants, the adjacent vertebra beyond the end of the second rod member 42" is not exposed to potentially impacting a rod section that would have previously extended longitudinally beyond pedicle screw location. This can reduce patient pain and increase patient mobility. A further advantage is that the smaller profile results in less tissue displacement in the vicinity of second rod member 42".

Figure 28:
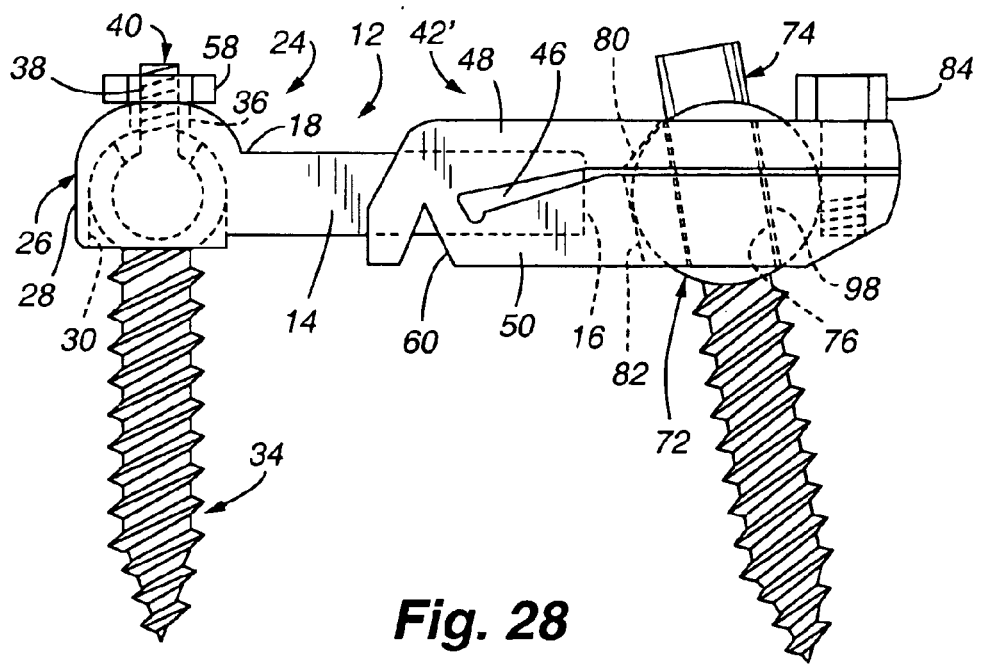
FIG. 28 is a side elevation view of one assembly that incorporates aspects of the present invention, wherein the assembly includes a first embodiment of a first rod member, a second embodiment of a second rod member.

Yet a separate aspect of the present invention is that different possible assemblies are available to meet a particular patient's needs. Referring now to FIG. 28, an implant assembly is shown that includes first rod member 12 in combination with a second rod member 42'. This combination allows for a polyaxial pedicle screw 34 to be used with a pedicle screw having a straight upper shank portion, such as pedicle screw 74 that is shown on the right side of the figure.

Figure 29:
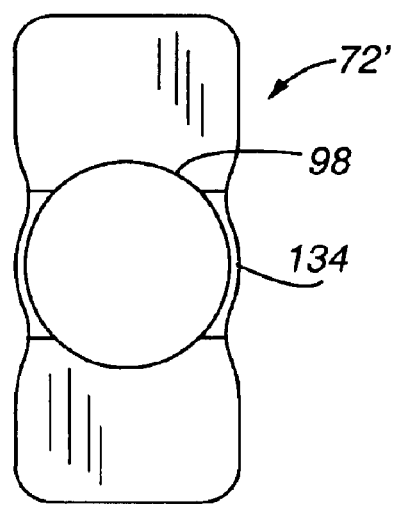
FIG. 29 is a plan view of a second embodiment of a deformable connector, wherein the deformable connector has a skeletonized structure.
Figure 30:
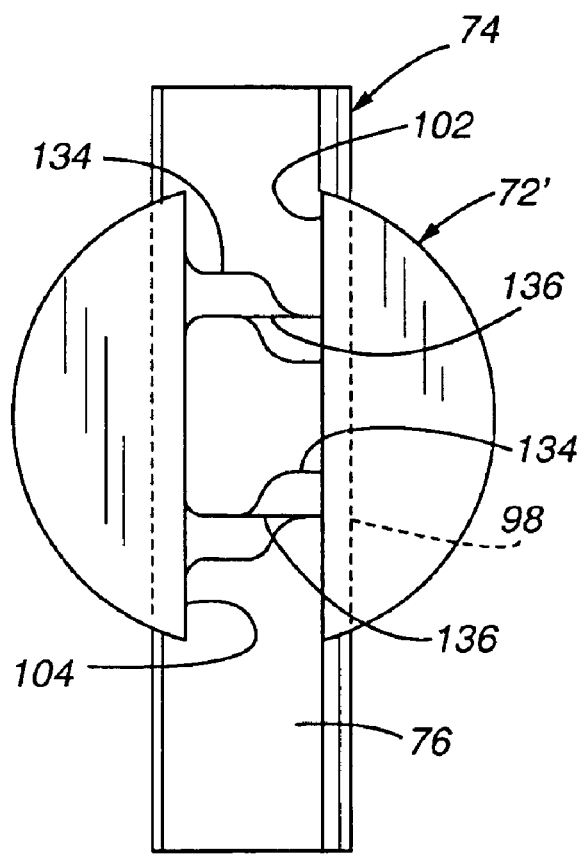
FIG. 30 is a side elevation view of the deformable connector shown in FIG. 29, in combination with a pedicle screw having a substantially straight upper shank portion.

Referring now to FIG. 29, a modified deformable connector 72' is shown wherein the deformable connector 72' has a skeletonized structure to reduce its weight. As shown in FIG. 29, in a preferred embodiment, the skeletonized structure of the deformable connector 72' can take the form of one or more tie beams 134 that structurally tie together portions of the deformable connector 72'. The tie beam 134 may include a textured surface 136 with, for example, a ridged, grooved or roughened surface for allowing the tie beam 134 to be selectively adjusted during the tightening process. The deformable connector 72' can be formed of a structural frame that is partially compressible to lock the pedicle screw 74 in place and prevent its rotation after a tightening force is applied using a tightening member 84.

The exterior surface of the beam 14, such as the top side 20 and the bottom side 22 may possess surface features that interlock and aid in securing the beam 14 to the inside of the second rod member 42. Similarly, the inside surfaces of the second rod member 42, 42' and/or 42", such as the interior surfaces 54 and/or 56 of the upper arm 48 and lower arm 50, respectively, may also include features that interlock and aid in securing the beam 14 within the second rod member 42. For example, the various previously identified surfaces may include detents or depressions that receivingly accept other structural features. Surficial features may include texturing, ridges, bumps, projections, protrusions, indentations, adhesives, and coverings or coatings of alternate materials. In addition, although not required, at least one set screw could be used to interlock the beam 14 to the second rod member 42, 42' and/or 42".

In a separate aspect of the invention, although the second rod members 42, 42', and 42" are preferably a one-piece, monolithic structure, they may be manufactured, assembled, or implanted in plurality of pieces. By way of example and not limitation, a multi-piece second rod member 42, 42', and 42" can include an upper arm 48 separately and/or hingedly connected to the lower arm 50. Such a structure may be desirable to allow easy insertion of a deformable connector 72 or 72' within a cavity 78 of a second rod member 42' and 42" during the manufacturing process.

The devices and structural features described herein are made from a material that possesses the appropriate strength characteristics necessary to withstand loading from the human body when used in medical applications. Tensile strength qualities of the materials used is a key consideration. Preferably, materials may include ceramics, plastics, metals, or carbon fiber composites. More preferably, the materials are made from titanium, a titanium alloy, or stainless steel.

Devices disclosed herein can also be made of thermal memory materials or materials that possess different elastic properties at varying temperatures. In this aspect of the invention, the subject component(s) may be heated or cooled to a desired temperature, implanted, then subsequently allowed to cool or warm to the temperature of the ambient conditions that will exist during the usage period for the subject device, namely, normal body temperature.

The dimensions of the devices disclosed herein are expected to vary depending upon the patient's needs. For example, a rod the entire length of the spine, such as 2 feet in length, may be used. Alternately, a rod only 10 to 40 mm long may be all that is necessary to span and bridge a disc of the spine. Therefore, for spinal applications, the preferable length of rod is simply an adequate length to bridge the necessary vertebral disc or discs. As a separate example, the beams of the first rod members described herein are anticipated to have a diameter of about 3–7 mm if solid and circular in cross section, and on the order of about 4–7 mm in length in the long dimension if solid and oblong in cross section. Again, the size of the dimensions of the devices is subject to the material used to construct the subject device, the intend use, and the specific characteristics of the patient. For example, a large person may have larger sized components than a device implanted in a child.

The curvature of the rod may also be variable depending upon the desired final curvature sought for the patient. The curvature may be established during manufacture of a given rod, and/or a given rod segment may have its curvature adjusted at the of time surgery prior to implantation.

The devices disclosed herein also have application to uses other than those specifically discussed. For example, one or more of the devices described herein have application to uses outside of surgical stabilization. For example, the devices could be used to connect framing of objects such as furniture. Even within the field of medicine and spinal surgery, one anticipated use involves using certain components described herein to cross-link or structurally interconnect right and left stabilization assemblies that are implanted on either side of a spinous process.

While various embodiments of the present invention have been described in detail, it is apparent that modifications and adaptations of those embodiments will occur to those skilled in the art. However, it is to be expressly understood that such modifications and adaptations are within the spirit and scope of the present invention, as set forth in the following claims.

What is claimed is:

1. A spinal rod implant for spanning at least one intervertebral disc, the implant interconnectable to a first vertebra using a first pedicle screw and to a second vertebra using a second pedicle screw, the first pedicle screw separated from the second pedicle screw by a bridge distance, the implant comprising:
   a first rod member for interconnecting to the first vertebra, said first rod member including a beam, said beam having an effective length shorter than the bridge distance;
   a second rod member for interconnecting to the second vertebra, said second rod member including a clamp sized to receive at least a portion of said beam, said clamp having an effective length shorter than the bridge distance; and
   means for tightening said clamp to create a force to secure said beam within said clamp.

2. The implant as claimed in claim 1, wherein said clamp includes an interior hollow chamber for receiving said at least a portion of said beam.

3. The implant as claimed in claim 1, wherein said clamp is of one-piece construction.

4. The implant as claimed in claim 1, wherein said clamp includes a deformable upper arm and wherein said means for tightening at least partially compresses said upper arm against said beam.

5. The implant as claimed in claim 4, wherein said clamp further includes a lower arm wherein said means for tightening at least partially compresses said beam against said lower arm.

6. The implant as claimed in claim 5, wherein said clamp further includes a slot, wherein said slot bisects a portion of said clamp and wherein said upper arm is spaced apart from said lower arm.

7. The implant as claimed in claim 1, wherein said clamp further includes an aperture for receiving said beam.

8. The implant as claimed in claim 7, wherein said clamp further includes a notch spaced apart from said aperture.

9. The implant as claimed in claim 7, wherein said aperture has a circular shape.

10. The implant as claimed in claim 7, wherein said aperture has non-circular shape.

11. The implant as claimed in claim 1, wherein said beam has a circular cross section.

12. The implant as claimed in claim 1, wherein said beam has a non-circular cross section.

13. The implant as claimed in claim 1, wherein said first rod member has a longitudinal axis substantially coincident with a longitudinal axis of said second rod member.

14. The implant as claimed in claim 1, wherein said means for tightening does not include a set screw.

15. The implant as claimed in claim 1, wherein said means for tightening comprises an end connector operatively associated with the second pedicle screw.

16. A bone stabilization assembly for securing a first bone segment to a second bone segment, comprising:
   first bone screw attachable to the first bone segment and a second bone screw attachable to the second bone segment;
   a first rod member including a beam and an end connector, said end connector attachable to said first bone screw;
   a second rod member including an interior hollow chamber for longitudinally receiving at least a portion of said beam, said second rod member including an upper arm and an opposing lower arm, said upper arm and said lower arm spaced apart by a slot wherein said slot is contiguous with said interior hollow chamber, and wherein said upper arm is moveable to contact said beam and compress said beam between said upper arm and said lower arm, said second rod member including a connector attachable to said second bone screw;
   means for tightening said second rod member to secure said beam within said second rod member.

17. The bone stabilization assembly of claim 16, wherein said means for tightening forces said connector of said second rod member to secure said second rod member to said second bone screw.

18. The bone stabilization assembly of claim 16, wherein said connector of said second rod member comprises a socket.

19. The bone stabilization assembly of claim 16, wherein said connector of said second rod member comprises a deformable connector.

20. The bone stabilization assembly of claim 19, wherein said deformable connector is disc-shaped.

21. A method of interconnecting a first vertebra to a second vertebra, the method comprising the steps of:
   (a) attaching a first pedicle screw to the first vertebra and a second pedicle screw to the second vertebra;
   (b) inserting a beam of a first rod member into a second rod member, the second rod member including an interior hollow chamber for longitudinally receiving at least a portion of the beam, the second rod member including an upper arm and an opposing lower arm, the upper arm and the lower arm spaced apart by a slot wherein the slot is contiguous with the interior hollow chamber, wherein the upper arm is moveable to contact the beam and compress the beam between the upper arm and the lower arm, and wherein the second rod member includes an integral connector for attaching the second rod member to the second pedicle screw;

(c) connecting the first rod member to the first pedicle screw using a connector interconnected to the beam; and (d) advancing a single tightening mechanism to secure:
  (i) the second rod member to the beam of the first rod member, and
  (ii) the second rod member to the second pedicle screw.

22. The method as claimed in claim 21, wherein the tightening mechanism is a tightening screw in the second rod member.

23. The method as claimed in claim 21, wherein the tightening mechanism is a tension link nut threaded onto a tension link shaft.

* * * * *